US006551584B2

(12) United States Patent
Bandyopadhyay et al.

(10) Patent No.: US 6,551,584 B2
(45) Date of Patent: Apr. 22, 2003

(54) TOPICAL ANTIBIOTIC COMPOSITION FOR TREATMENT OF EYE INFECTION

(75) Inventors: Rebanta Bandyopadhyay, Portage, MI (US); Pamela J. Secreast, Portage, MI (US); Leslie C. Hawley, Kalamazoo, MI (US); Vincent E. McCurdy, Portage, MI (US); Praveen Tyle, Kalamazoo, MI (US); Paramita Bandyopadhyay, Portage, MI (US); Satish Kumar Singh, Portage, MI (US)

(73) Assignee: Pharmacia & Upjohn Company, St. Louis, MO (US)

( * ) Notice: Subject to any disclaimer, the term of this patent is extended or adjusted under 35 U.S.C. 154(b) by 0 days.

(21) Appl. No.: 09/974,598

(22) Filed: Oct. 10, 2001

(65) Prior Publication Data

US 2002/0107238 A1 Aug. 8, 2002

Related U.S. Application Data

(60) Provisional application No. 60/239,136, filed on Oct. 10, 2000, and provisional application No. 60/285,340, filed on Apr. 20, 2001.

(51) Int. Cl.[7] .............................................. A61K 31/74
(52) U.S. Cl. ................................................... 424/78.04
(58) Field of Search ............................ 424/78.04, 427

(56) References Cited

U.S. PATENT DOCUMENTS

| 3,453,259 A | 7/1969 | Parmerter et al. ........... 260/209 |
| 3,863,633 A | 2/1975 | Ryde et al. .................. 128/260 |
| 3,867,519 A | 2/1975 | Michaels ..................... 424/19 |
| 3,868,445 A | 2/1975 | Ryde et al. ................... 424/14 |
| 3,914,402 A | 10/1975 | Shell ............................ 424/32 |
| 3,960,150 A | 6/1976 | Hussain et al. .............. 128/260 |
| 3,963,025 A | 6/1976 | Whitaker et al. ............ 128/260 |
| 3,991,759 A | 11/1976 | Urquhart ..................... 128/260 |
| 4,014,335 A | 3/1977 | Arnold ........................ 128/260 |
| 4,057,619 A | 11/1977 | Higuchi et al. ............... 424/14 |
| 4,186,184 A | 1/1980 | Zaffaroni ..................... 424/14 |
| 4,281,654 A | 8/1981 | Shell et al. .................. 128/260 |

(List continued on next page.)

FOREIGN PATENT DOCUMENTS

| EP | 0424 043 B1 | 5/1993 |
| WO | WO 95/03784 | 2/1995 |
| WO | WO 96/06581 | 3/1996 |
| WO | WO 96/32135 | 10/1996 |
| WO | WO 98/55148 | 12/1998 |
| WO | WO 98/58677 | 12/1998 |
| WO | WO 99/24396 | 5/1999 |
| WO | WO 99/43333 | 9/1999 |
| WO | WO 00/03710 | 1/2000 |
| WO | WO 00/18387 | 4/2000 |
| WO | WO 01/19366 | 3/2001 |

OTHER PUBLICATIONS

Rajewski & Stella. Journal of Pharmaceutical Sciences. 85, 1155–1159. (1996).
Loftsson. Pharmazie. 53, 733–740. (1998).
Sorensen & Jensen. Acta Ophthalmol. 57, 564–581. (1979).

Primary Examiner—Carlos Azpuru
(74) Attorney, Agent, or Firm—Karen B. King; James C. Forbes

(57) ABSTRACT

There is provided a pharmaceutical composition suitable for topical administration to an eye, the composition comprising as active agent at least one oxazolidinone antibacterial drug, for example linezolid, in a concentration effective for treatment and/or prophylaxis of a gram-positive bacterial infection of an eye, and at least one ophthalmically acceptable excipient ingredient that reduces a rate of removal of the composition from the eye by lacrimation such that the composition has an effective residence time in the eye of about 2 to about 24 hours. The composition is, for example, an in situ gellable solution, suspension or solution/suspension.

29 Claims, 2 Drawing Sheets

U.S. PATENT DOCUMENTS

| | | | |
|---|---|---|---|
| 4,303,637 A | 12/1981 | Shell et al. | 424/14 |
| 4,474,751 A | 10/1984 | Haslam et al. | 424/78 |
| 4,478,818 A | 10/1984 | Shell et al. | 424/14 |
| 4,559,343 A | 12/1985 | Han et al. | 514/264 |
| 4,861,760 A | 8/1989 | Mazuel et al. | 514/54 |
| 4,911,920 A | 3/1990 | Jani et al. | 424/78 |
| 5,134,127 A | 7/1992 | Stella et al. | 514/58 |
| 5,164,510 A | 11/1992 | Brickner | 548/231 |
| 5,190,927 A | 3/1993 | Chang et al. | 514/54 |
| 5,192,535 A | 3/1993 | Davis et al. | 424/78.04 |
| 5,212,162 A | 5/1993 | Missel et al. | 514/54 |
| 5,231,188 A | 7/1993 | Brickner | 548/221 |
| 5,275,820 A | 1/1994 | Chang | 424/426 |
| 5,376,645 A | 12/1994 | Stella et al. | 514/58 |
| 5,403,841 A | 4/1995 | Lang et al. | 514/226.8 |
| 5,443,505 A | 8/1995 | Wong et al. | 623/4 |
| 5,565,571 A | 10/1996 | Barbachyn et al. | 546/144 |
| 5,587,175 A | 12/1996 | Viegas et al. | 424/427 |
| 5,627,181 A | 5/1997 | Riedl et al. | 514/236.8 |
| 5,652,238 A | 7/1997 | Brickner et al. | 514/235.8 |
| 5,688,791 A | 11/1997 | Kimura et al. | 514/224.5 |
| 5,688,792 A | 11/1997 | Barbachyn et al. | 514/235.5 |
| 5,698,574 A | 12/1997 | Biedl et al. | 514/376 |
| 5,837,870 A | 11/1998 | Pearlman et al. | 544/137 |
| 5,869,079 A | 2/1999 | Wong et al. | 424/426 |
| 5,874,418 A | 2/1999 | Stella et al. | 514/58 |
| 5,876,744 A | 3/1999 | Della Valle et al. | 424/434 |
| 6,046,177 A | 4/2000 | Stella et al. | 514/58 |
| 6,069,145 A | 5/2000 | Betts | 514/252 |
| 6,133,248 A | 10/2000 | Stella | 514/58 |
| 2002/0035264 A1 * | 3/2002 | Kararli et al. | 546/300 |

* cited by examiner

TOPICAL ANTIBIOTIC COMPOSITION FOR TREATMENT OF EYE INFECTION

This application claims the benefit of U.S. Provisional Patent Application No. 60/239,136, filed Oct. 10, 2000, and of U.S. Provisional Patent Application No. 60/285,340, filed Apr. 20, 2001.

FIELD OF THE INVENTION

The present invention relates to a pharmaceutical composition useful for topical application to an eye for treatment or prevention of infective disease of the eye. In particular, the present invention relates to an ophthalmic formulation of an oxazolidinone antibiotic that can be applied to the eye for treatment or prevention of ophthalmic infection by a gram-positive bacterial agent. The field of the present invention also includes therapeutic or prophylactic use of such a formulation, and use of such a formulation in preparation of a medicament.

BACKGROUND OF THE INVENTION

Numerous oxazolidinone compounds have been reported having therapeutically and/or prophylactically useful antibiotic, in particular antibacterial, effect. Among such compounds are those illustratively disclosed in the following patents, each of which is individually incorporated herein by reference.

U.S. Pat. No. 5,164,510 to Brickner.
U.S. Pat. No. 5,231,188 to Brickner.
U.S. Pat. No. 5,565,571 to Barbachyn & Brickner.
U.S. Pat. No. 5,627,181 to Riedl et al.
U.S. Pat. No. 5,652,238 to Barbachyn et al.
U.S. Pat. No. 5,688,792 to Barbachyn et al.
U.S. Pat. No. 5,698,574 to Riedl et al.
U.S. Pat. No. 6,069,145 to Betts.

Compounds disclosed in above-cited U.S. Pat. No. 5,688,792 include for example the compound (S)-N-[[3-[3-fluoro-4-(4-morpholinyl)phenyl]-2-oxo-5-oxazolidinyl]methyl]acetamide, also referred to herein as linezolid. Linezolid has the structure shown in formula (I):

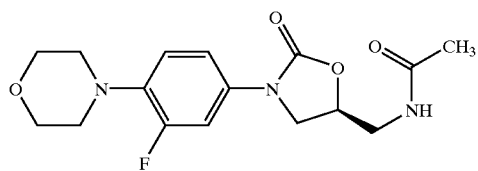

and is in commercial use as a medicament under the trademark Zyvox® of Pharmacia Corporation. Linezolid exhibits strong antibacterial activity against gram-positive organisms including those of the following genera: Staphylococcus (e.g., *Staphylococcus aureus, Staphylococcus epidermidis*), Streptococcus (e.g., *Streptococcus viridans, Streptococcus pneumoniae*), Enterococcus, Bacillus, Corynebacterium, Chlamydia and Neisseria. Many such gram-positive organisms have developed significant levels of resistance to other antibiotics. About 65% of all cases of bacterial keratitis and about 85% of all cases of bacterial conjunctivitis are attributable to infection by gram-positive organisms such as those listed above.

Above-cited U.S. Pat. No. 5,688,792 discloses that the subject antibiotic oxazolidinone compounds, including linezolid, can be formulated as a gel or cream for topical application to skin.

International Patent Publication No. WO 00/03710, incorporated herein by reference, discloses a method of treating bacterial keratitis or bacterial conjunctivitis in an eye, comprising topical administration of an oxazolidinone antibiotic to the infected eye. Preferred oxazolidinone compounds for use according to the method of WO 00/03710 include (S)-N-[[3-[3-fluoro-4-(4-morpholinyl)phenyl]-2-oxo-5-oxazolidinyl]methyl]acetamide (linezolid) and (S)-N-[[3-[3-fluoro-4-[4-(hydroxyacetyl)-1-piperazinyl]]phenyl]-2-oxo-5-oxazolidinyl]methyl]acetamide (eperezolid). The oxazolidinone compound is said to be administered in a formulation such as a solution, cream, ointment, emulsion, suspension or slow release formulation, a solution being preferred. Formulations exemplified include 10% and 12% weight/volume solutions of linezolid. It is suggested that the formulation be administered 2–4 times daily for 7–10 days or until the infection is gone, and that preferably about 1 drop to about 5 drops of the formulation are administered each time. It is further disclosed in WO 00/03710 that the oxazolidinone compound can be used individually, in combination with another oxazolidinone compound, in combination with other antibacterial agents, or in combination with non-antibacterial agents.

International Patent Publication No. WO 00/18387, incorporated herein by reference, discloses ophthalmic compositions comprising an oxazolidinone antimicrobial agent. Preferred oxazolidinone compounds according to WO 00/18387 are those of above-cited U.S. Pat. No. 5,627,181. Optionally the compositions can further comprise an anti-inflammatory agent. Typically 1–4 drops of a solution or suspension, or a comparable amount of an ointment, gel or other solid or semisolid composition, are said to be applied 1–4 times a day.

A challenge for topical administration of drugs to the eye is a high rate of drug loss from the exterior of the eye. Only a small volume of fluid can be accommodated in the exterior of the eye, including the conjunctival sac, and under normal conditions lacrimal fluid fills most of the available volume. The additional volume of fluid in the form of a drug formulation that can be accepted by a human eye without washout varies from about 3 µl to about 25 µl, but is normally about 10 µl. Furthermore, turnover rate of lacrimal fluid is high, typically about 16% per minute, and this can lead to rapid loss of an instilled drug by normal lacrimal drainage. Thus under normal conditions, only about 10% to about 20% of a drug dose is retained in the exterior of the eye 5 minutes after placement therein of 1–2 drops of a solution or suspension composition of the drug, and the composition is almost completely eliminated within 15 minutes. See for example Sorensen & Jensen (1979), *Acta Ophthalmol.* (Copenhagen) 57, 564–581. Reflex blinking and lacrimation caused by irritation from the topical administration can result in even faster drug loss.

Increasing viscosity of the instilled formulation and hence of the lacrimal fluid can reduce the rate of lacrimal drainage and thereby increase residence time of the drug in the exterior of the eye. Ointments are often used for this reason; however, ointments often cause discomfort by interfering with vision and free movement of the eyelids. Clear aqueous solutions and suspensions are therefore usually a preferred choice, especially for daytime administration.

U.S. Pat. No. 3,867,519 to Michaels, incorporated herein by reference, discloses a device for delivering a drug at a controlled rate to an eye, the device comprising an inner reservoir of the drug confined in a biodegradable matrix and an outer bioerodible membrane through which the drug passes into the eye.

U.S. Pat. No. 3,914,402 to Shell, incorporated herein by reference, discloses an ophthalmic dosage form comprising solid particles of a drug enclosed within a bioerodible polymer such as a polyester, cross-linked gelatin or a polycarboxylic acid. The polymer is said to gradually erode in the eye, releasing the drug at a controlled rate.

U.S. Pat. No. 3,960,150 to Hussain et al., incorporated herein by reference, discloses a bioerodible ocular insert containing a drug. Through erosion of the ocular insert in the eye, the drug is said to be released at a controlled rate.

U.S. Pat. No. 3,963,025 to Whitaker & Gad, incorporated herein by reference, discloses a bioerodible ocular drug delivery device said to have improved retention in an eye.

U.S. Pat. No. 4,014,335 to Arnold, incorporated herein by reference, discloses an ocular drug delivery device comprising a shaped body having a drug reservoir enclosed by walls, one of which is formed of a material that is permeable to the drug and controls the release rate of the drug.

U.S. Pat. No. 4,057,619 to Higuchi & Hussain, incorporated herein by reference, discloses an ocular drug delivery system comprising an ethylene-vinyl ester copolymer through which a drug can diffuse.

U.S. Pat. No. 4,186,184 to Zaffaroni, incorporated herein by reference, discloses an ocular drug delivery system that can be inserted in an eye and that has a drug-releasing portal which can be oriented towards a preselected tissue of the eye for controlled release of the drug thereto.

U.S. Pat. No. 4,474,751 to Haslam et al., incorporated herein by reference, discloses liquid aqueous ophthalmic compositions comprising a drug, preferably a water-soluble drug, together with 10% to 50% by weight of a thermosetting polymer that forms a gel at a human body temperature. Upon placement of such a liquid composition in an eye, a gel is said to form thereby retarding loss of the drug from the eye by lacrimal drainage. Such compositions are said to be useful for ophthalmic delivery of antibacterial agents, for example vancomycin.

U.S. Pat. No. 4,861,760 to Mazuel & Friteyre, incorporated herein by reference, discloses a liquid in situ gelling composition said to be suitable for ophthalmic use. The composition contains in aqueous solution a polysaccharide that undergoes liquid-gel phase transition in response to ionic strength of tear fluid. A suitable polysaccharide is gellan gum, which can be used in a concentration of 0.1% to 2% by weight of the composition. Such a composition is said to be useful for ophthalmic delivery of antibacterial agents, for example vancomycin.

U.S. Pat. No. 5,192,535 to Davis et al., incorporated herein by reference, discloses liquid compositions said to be suitable for use as eye drops, utilizing a different in situ gelling mechanism. These compositions contain a lightly cross-linked carboxyl-containing polymer such as polycarbophil and have a pH of about 3.0 to about 6.5. Upon placement of such a composition in an eye, contact with lacrimal fluid having a pH of about 7.2 to about 7.4 is said to result in gelling and consequent increase of residence time in the eye, permitting sustained release of a drug contained in the composition. Drugs for which such a composition is said to be useful include antibiotics, for example vancomycin.

U.S. Pat. No. 5,212,162 to Missel et al., incorporated herein by reference, discloses further liquid in situ gelling compositions said to be suitable for ophthalmic use. The compositions contain a drug together with a finely-divided (conveniently about 1 to about 25 µm particle size) carrier that binds with the drug, and a gelling polysaccharide, preferably a carrageenan, especially a carrageenan having not more than 1.0 sulfate moiety per disaccharide unit, e.g., eucheuma carrageenan, kappa-carrageenan or furcellaran. Such compositions are said to be useful for ophthalmic delivery of anti-infective agents, for example ciprofloxacin.

U.S. Pat. No. 5,403,841 to Lang et al., incorporated herein by reference, discloses further liquid in situ gelling compositions said to be suitable for ophthalmic use. These compositions contain a carrageenan having not more than 1.0 sulfate moiety per disaccharide unit that is capable of gelling in 0.5% to 1.0% aqueous sodium chloride solution. Such compositions are said to be useful for ophthalmic delivery of anti-infective agents, for example ciprofloxacin.

U.S. Pat. No. 5,587,175 to Viegas et al., incorporated herein by reference, discloses further liquid in situ gelling compositions said to be suitable for ophthalmic use. These compositions contain an ionic polysaccharide, for example gellan gum, alginate gum or chitosan, and a film-forming agent, for example hydroxypropyl methylcellulose, carboxymethylcellulose, sodium chondroitin sulfate, sodium hyaluronate, polyvinylpyrrolidone, etc. The compositions are pH buffered to match pH of tear fluid. Gelling is said to occur upon contact with calcium ions. Such compositions are said to be useful for ophthalmic delivery of antibacterial agents, for example vancomycin.

U.S. Pat. No. 5,869,079 to Wong & Kochinke, incorporated herein by reference, discloses a biodegradable ocular implant comprising a hydrophobic entity such as a lactic/glycolic acid polyester and a hydrophilic entity such as hydroxypropylmethylcellulose, this combination of entities being said to modulate each other's release and that of a drug contained therewithin.

U.S. Pat. No. 5,876,744 to Della Valle et al., incorporated herein by reference, discloses bioadhesive and mucoadhesive compositions, including some said to be useful as ophthalmic compositions, comprising mixtures of synthetic polymers such as polycarbophil and polyvinyl alcohol and biopolymers such as alginic acid, hyaluronic acid and dermatan sulfate. Such compositions are said to be capable of increasing contact time with a treated eye of specific drugs.

European Patent No. 0 424 043, incorporated herein by reference, discloses a liquid ophthalmic composition comprising a sulfated polysaccharide or derivative thereof that undergoes a liquid-gel transition on interaction with proteins of the lacrimal fluid in the eye. Such sulfated polysaccharides are said to include kappa-carrageenan, iota-carrageenan and mixtures thereof. The composition is said to be useful for ophthalmic delivery of antibacterial agents.

None of the references cited above specifically contemplates formulating an oxazolidinone antibiotic in a composition exhibiting prolonged residence time in a treated eye. None of the references cited above specifically contemplates such a composition further comprising a preservative. None of the references cited above leads one of skill in the art to expect a problem in preparing such a composition that does not contain solid particulates, or to find a solution to such a problem. None of the references cited above specifically contemplates a combination therapy or coformulation of an oxazolidinone antibacterial agent having a high degree of activity against gram-positive bacteria with one or more antibacterial agents effective against gram-negative bacteria.

A need remains for a composition of an oxazolidinone antibiotic drug suitable for topically treating and/or preventing bacterial infections of the eye, that delivers the drug continuously to the eye over a prolonged period of time, for example over at least about 2 hours, preferably longer. A particular need remains for such a composition further comprising a preservative. A further particular need remains for such a composition that is substantially free of solid particulates that could cause discomfort and/or irritation to a treated eye. Furthermore, a need remains for an ophthalmically acceptable co-therapy or coformulation that is effective against both gram-negative organisms and gram-positive organisms, particularly gram-positive organisms that have become resistant to most antibiotics.

One or more of these needs will be seen to be met by the invention now described.

SUMMARY OF THE INVENTION

The present invention provides a pharmaceutical composition suitable for topical administration to an eye, the composition comprising as active agent one or more oxazolidinone antibacterial drugs in a concentration effective for treatment and/or prophylaxis of a gram-positive bacterial infection of one or more tissues of the eye, and one or more ophthalmically acceptable excipient ingredients that reduce rate of removal of the composition from the eye by lacrimation such that the composition has an effective residence time in the eye of about 2 to about 24 hours.

Lacrimation is the production of tear fluid, and can remove matter from the eyes both by external wash-out and by lacrimal drainage into the nasopharyngeal cavity via the nasolacrimal ducts. A consequence of removal of an ophthalmic composition from a treated eye is a reduced concentration of the active agent in the lacrimal fluid and hence in the target tissue.

For sustained antibacterial action, the concentration in the lacrimal fluid and in the target tissue, e.g., the conjunctiva or the cornea, must remain above the $MIC_{90}$ for the active agent in question. The $MIC_{90}$ is the minimum inhibitory concentration for 90% of the target organisms, in this instance infective gram-positive bacteria. For example, where the active agent is linezolid, the $MIC_{90}$ is about 4 $\mu$g/ml. By "effective residence time" herein is meant a period of time following application of the composition to the eye during which the concentration of the active agent in the lacrimal fluid and/or in the target tissue remains above the $MIC_{90}$ for that active agent.

The composition therefore provides sustained antibacterial action over a period of at least about 2 hours.

The invention also provides a method of preparing a medicament for treating or preventing a gram-positive bacterial infection in an eye, using a composition as described above.

Also embraced by the present invention is a method of treating or preventing a gram-positive bacterial infection in an eye, the method comprising application to the eye of a composition as described above in a therapeutically or prophylactically effective dose.

Furthermore, the present invention provides a method of treating or preventing both gram-positive and gram-negative bacterial infections in an eye, the method comprising topical application to the eye in co-therapy (including coformulation) one or more oxazolidinone antibiotics and one or more antibiotics effective against gram-negative organisms. "Co-therapy" herein means administration topically to the eye, at the same time or sequentially, of an ophthalmically acceptable composition of the oxazolidinone (s) and a separate ophthalmically acceptable composition of the gram-negative effective antibiotic(s), in a treatment regimen intended to provide a beneficial effect from co-action of the two types of antibiotic. "Coformulation" herein means that the oxazolidinone(s) and the gram-negative effective antibiotic(s) are administered topically to the eye as components of a single ophthalmically acceptable composition.

In one embodiment of the invention, a composition as described herein is used topically in treatment of an existing bacterial infection. Infective diseases of the eye for which compositions and methods of the invention are useful include without limitation conjunctivitis, keratitis, blepharitis, blepharoconjunctivitis, orbital and preseptal cellulitis and endophthalmitis. In preferred methods the infected tissue is one that is directly bathed by the lacrimal fluid, as in conjunctivitis, keratitis, blepharitis and blepharoconjunctivitis.

In infective diseases of the eye where the causal organism is non-bacterial, there can be benefit in prophylactic use of a composition of the invention to control secondary bacterial infections. Examples of such situations include conjunctivitis and keratitis of viral etiology, e.g., adenoviral conjunctivitis, molluscum contagiosum, herpes simplex conjunctivitis and keratitis, etc., and fungal keratitis.

Prophylactic uses of a composition of the invention also include post-traumatic prophylaxis, especially post-surgical prophylaxis, and prophylaxis prior to ocular surgery.

What constitutes a "concentration effective for treatment and/or prophylaxis of a gram-positive bacterial infection" depends, among other factors, on the particular oxazolidinone compound or compounds being administered; the residence time provided by the particular formulation of the active agent; the species, age and body weight of the subject; the particular ophthalmic condition for which treatment or prophylaxis is sought; and the severity of the condition. In the case of linezolid, an effective concentration in a composition of the invention for topical administration to an eye will generally be found in the range from about 0.01% to about 20%, more typically about 0.05% to about 8%, weight/volume. For oxazolidinone compounds other than linezolid, an appropriate concentration range is one that is therapeutically equivalent to the linezolid concentration range indicated above.

A composition of the invention is conveniently but not necessarily formulated as an in situ gellable aqueous liquid, and can be administered as eye drops. Typically each drop, generated by a conventional dispensing means, has a volume of about 10 to about 40 $\mu$l. From 1 to about 6 such drops typically provides a suitable dose of the oxazolidinone active agent. Where the composition is administered in a form other than eye drops, for example as an ophthalmic ointment or as a solid implant, an equivalent dose is provided. Such a dose can be administered as needed, but typically administration to the eye 1 to about 6 times per day, in most cases 2 to 4 times a day, provides adequate continuing relief or prevention of the infective disease indicated.

The term "ophthalmically acceptable" with respect to a formulation, composition or ingredient herein means having no persistent detrimental effect on the treated eye or the functioning thereof, or on the general health of the subject being treated. It will be recognized that transient effects such as minor irritation or a "stinging" sensation are common with topical ophthalmic administration of drugs and the existence of such transient effects is not inconsistent with the formulation, composition or ingredient in question being "ophthalmically acceptable" as herein defined. However, preferred formulations, compositions and ingredients are those that cause no substantial detrimental effect, even of a transient nature.

Contemplated compositions are highly effective in treating gram-positive bacterial infections of the eye. Without being bound by theory, it is believed that the prolonged residence time exhibited by compositions of the invention is responsible at least in part for their superior effectiveness. In a topical administration method as provided by the present invention, the dosage of the active agent is generally much lower than would typically be administered orally to provide a therapeutically or prophylactically effective blood serum concentration.

The concentration of the active agent in an ophthalmic composition of the invention can also be much lower than that exemplified for a topically applied simple solution formulation of an oxazolidinone antibiotic. For example, above-cited International Patent Publication No. WO 00/03710 discloses in Example 6 thereof a treatment for bacterial keratitis, wherein a 10% (100 mg/ml) solution of linezolid is dropped on the surface of the eye in an amount of 3–5 drops, 4 times a day; and in Example 7 thereof a treatment for bacterial conjunctivitis, wherein a 12% (120 mg/ml) solution of linezolid is dropped on the surface of the eye in an amount of 3 drops, 3 times a day. By contrast, a preferred composition of the present invention can be effective at a linezolid concentration of about 0.5 to about 80 mg/ml, more preferably about 0.5 to about 50 mg/ml, still more preferably about 0.5 to about 20 mg/ml, and most preferably about 0.5 to about 10 mg/ml, for example about 2 to about 2.5 mg/ml.

The very low dose permitted by the composition and method of the invention is a major advantage of the invention. Topical application as herein described, with greatly reduced drainage via the nasolacrimal duct into the gastrointestinal tract, avoids unnecessary systemic distribution of the oxazolidinone antibiotic throughout the body, and thereby reduces risk of development of resistant strains of gram-positive bacteria.

Other features and advantages of the invention will be in part apparent and in part pointed out hereinafter.

DETAILED DESCRIPTION OF THE INVENTION

Figure 1:
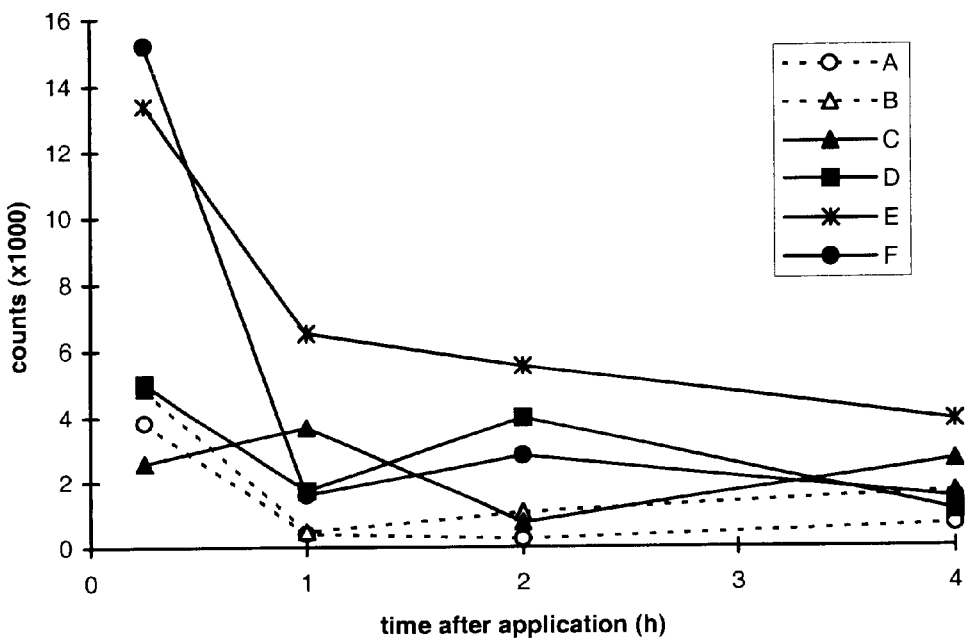
FIG. 1 is a graphical representation of data from Example 1, showing relative retention of $^{14}$C-linezolid (determined as radioactive counts) in guinea pig eyes following treatment with linezolid formulations A–F as described herein.

As indicated above, the invention provides a pharmaceutical composition suitable for topical administration to an eye. The composition comprises one or more oxazolidinone antibacterial drugs, preferably a single such drug, in a concentration effective for treatment and/or prophylaxis of a gram-positive bacterial infection in the eye, and one or more ophthalmically acceptable excipient ingredients that reduce rate of removal of the composition from the eye by lacrimation. The effect of the excipient ingredients in reducing rate of removal from the eye by lacrimation is to be understood as including rendering the composition resistant to removal from the eye by lacrimation. By virtue at least in part of this reduced rate of removal by lacrimation, the composition has an effective residence time in the eye of about 2 to about 24 hours.

A composition of the invention, upon topical application to an eye in accordance with the present invention, maintains a concentration of the oxazolidinone drug in the lacrimal fluid and/or in the target tissue, e.g., the conjunctiva, above the $MIC_{90}$ for at least about 2 hours. Preferably, the concentration remains above the $MIC_{90}$ for at least about 3 hours, more preferably at least about 4 hours and most preferably at least about 6 hours.

In a preferred embodiment, the oxazolidinone drug is a compound of formula (II)

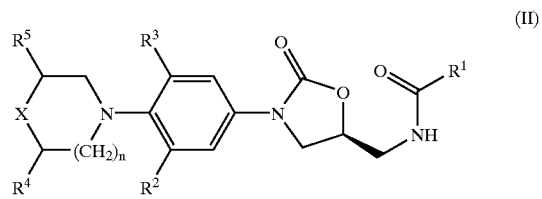

wherein:

$R^1$ is selected from (a) H, (b) $C_{1-8}$ alkyl optionally substituted with one or more F, Cl, OH, $C_{1-8}$ alkoxy, $C_{1-8}$ acyloxy or benzoxy groups, and including $C_{3-6}$ cycloalkyl, (c) amino, (d) mono- and di($C_{1-8}$ alkyl) amino and (e) $C_{1-8}$ alkoxy groups;

$R^2$ and $R^3$ are independently selected from H, F and Cl groups;

$R^4$ is H or $CH_3$;

$R^5$ is selected from H, $CH_3$, CN, $CO_2R^1$ and $(CH_2)_m R^6$ groups, where $R^1$ is as defined above, $R^6$ is selected from H, OH, $OR^1$, $OCOR^1$, $NHCOR^1$, amino, mono- and di($C_{1-8}$ alkyl)amino groups and m is 1 or 2;

n is 0, 1 or 2; and

X is O, S, SO, $SO_2$, $SNR^7$ or $S(O)NR^7$ where $R^7$ is selected from H, $C_{1-4}$ alkyl (optionally substituted with one or more F, Cl, OH, $C_{1-8}$ alkoxy, amino, $C_{1-8}$ mono- or di($C_{1-8}$ alkyl)amino groups), and p-toluenesulfonyl groups; or a pharmaceutically acceptable salt thereof.

Particularly preferred oxazolidinone drugs according to this embodiment are compounds of formula (II) wherein $R^1$ is $CH_3$; R and $R^3$ are independently selected from H and F but at least one of $R^2$ and R $^3$ is F; $R^4$ and $R^5$ are each H; n is 1; and X is O, S or $SO_2$. In another preferred embodiment, the oxazolidinone drug is selected from linezolid, eperezolid, N-((5S)-3-(3-fluoro-4-(4-(2-fluoroethyl)-3-oxopiperazin-1-yl)phenyl)-2-oxooxazolidin-5-ylmethyl)acetamide, (S)-N-[[3-[5-(3-pyridyl)thiophen-2-yl]-2-oxo-5-oxazolidinyl]methyl]acetamide, (S)-N-[[3-[5-(4-pyridyl)pyrid-2-yl]-2-oxo-5-oxazolidinyl]methyl] acetamide hydrochloride and N-[[(5S)-3-[4-(1,1-dioxido-4-thiomorpholinyl)-3,5-difluorophenyl]-2-oxo-5-oxazolidinyl]methyl]acetamide.

According to either of these preferred embodiments, an especially preferred oxazolidinone drug is linezolid. Another especially preferred oxazolidinone drug is N-[[(5S)-3-[4-(1, 1-dioxido-4-thiomorpholinyl)-3,5-difluorophenyl]-2-oxo-5- oxazolidinyl]methyl]acetamide. The invention is illustrated herein with particular reference to linezolid, and it will be understood that any other oxazolidinone antibacterial compound can, if desired, be substituted in whole or in part for linezolid, with appropriate adjustment in concentration and dosage ranges, in the compositions and methods herein described.

Oxazolidinone compounds used in compositions of the invention can be prepared by a process known per se, in the case of linezolid and eperezolid, for example, by processes described in the following patents, each of which is individually incorporated herein by reference.

U.S. Pat. No. 5,688,791.

U.S. Pat. No. 5,837,870.

International Patent Publication No. WO 99/24393.

Other oxazolidinone drugs can be prepared by processes known per se, including processes set forth in patent publications disclosing such drugs.

A composition of the invention can illustratively take the form of a liquid wherein the active agent is present in solution, in suspension or both. The term "solution/suspension" herein refers to a liquid composition wherein a first portion of the active agent is present in solution and a second portion of the active agent is present in particulate form, in suspension in a liquid matrix. A liquid composition herein includes a gel. Preferably the liquid composition is aqueous. Alternatively, the composition can take the form of an ointment.

As a further alternative, the composition can take the form of a solid article that can be inserted in a suitable location in the eye, such as between the eye and eyelid or in the conjunctival sac, where it releases the active agent as described, for example, in the patents listed below.

U.S. Pat. No. 3,863,633 to Ryde & Ekstedt, incorporated herein by reference.

Above-cited U.S. Pat. No. 3,867,519.

U.S. Pat. No. 3,868,445 to Ryde & Ekstedt, incorporated herein by reference.

Above-cited U.S. Pat. No. 3,960,150.

Above-cited U.S. Pat. No. 3,963,025.

U.S. Pat. No. 3,991,759 to Urquhart, incorporated herein by reference.

Above-cited U.S. Pat. No. 4,014,335.

Above-cited U.S. Pat. No. 4,057,619.

Above-cited U.S. Pat. No. 4,186,184.

U.S. Pat. No. 4,190,642 to Gale et al., incorporated herein by reference.

U.S. Pat. No. 4,281,654 to Shell & Gale, incorporated herein by reference.

U.S. Pat. No. 4,303,637 to Shell & Gale, incorporated herein by reference.

U.S. Pat. No. 4,478,818 to Shell & Gale, incorporated herein by reference.

U.S. Pat. No. 5,443,505 to Wong & Kochinke, incorporated herein by reference.

Above-cited U.S. Pat. No. 5,869,079.

Release from such an article is usually to the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in preparation of ocular implants carrying one or more oxazolidinone antibacterial drugs in accordance with the present invention include without restriction aliphatic polyesters such as polymers and copolymers of poly(glycolide), poly(lactide), poly($\epsilon$-caprolactone), poly(hydroxybutyrate) and poly(hydroxyvalerate), polyamino acids, polyorthoesters, polyanhydrides, aliphatic polycarbonates and polyether lactones. Illustrative of suitable non-bioerodible polymers are silicone elastomers.

In a presently preferred embodiment, the composition is an aqueous solution, suspension or solution/suspension, which can be presented in the form of eye drops. By means of a suitable dispenser, a desired dosage of the active agent can be metered by administration of a known number of drops into the eye. For example, for a drop volume of 25 $\mu$l, administration of 1–6 drops will deliver 25–150 $\mu$l of the composition. Suitable dispensers are illustratively disclosed in International Patent Publication No. WO 96/06581, incorporated herein by reference.

An aqueous suspension or solution/suspension of the invention can contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

However, in a particularly preferred embodiment, the composition is an aqueous solution having no substantial amount of solid particulate matter, whether of the drug, of an excipient or of both. Such solid particulate matter, if present, can cause discomfort and/or irritation of a treated eye.

The aqueous suspension or solution of the present invention is preferably viscous or mucoadhesive, or even more preferably, both viscous or mucoadhesive. In a particularly preferred embodiment, the aqueous suspension or solution/suspension of the invention contains carboxymethylcellulose, a viscosity enhancer and promoter of mucoadhesion. The concentration of carboxymethylcellulose in the aqueous suspension or solution of the present invention is preferably 0.1% to 5%, more preferably about 0.1% to about 2.5% by weight. The carboxymethylcellulose is preferably in the form of sodium carboxymethylcellulose substituted to a degree that the sodium content of the sodium carboxymethylcellulose is about 1% to about 20%.

Preferably no more than 3 drops, more preferably no more than 2 drops, and most preferably no more than 1 drop, each of about 10 to about 40 $\mu$l, preferably about 15 to about 30 $\mu$l, for example about 20 $\mu$l, should contain the desired dose of the active agent for administration to an eye. Administration of a larger volume to the eye risks loss of a significant portion of the applied composition by lacrimal drainage.

In a preferred embodiment, the composition is an in situ gellable aqueous composition, more preferably an in situ gellable aqueous solution. Such a composition comprises a gelling agent in a concentration effective to promote gelling upon contact with the eye or with lacrimal fluid in the exterior of the eye. Suitable gelling agents non-restrictively include thermosetting polymers such as tetra-substituted ethylene diamine block copolymers of ethylene oxide and propylene oxide (e.g., poloxamine 1307); polycarbophil; and polysaccharides such as gellan, carrageenan (e.g., kappa-carrageenan and iota-carrageenan), chitosan and algi- nate gums.

Aqueous compositions of the invention have ophthalmically compatible pH and osmolality. Preferably these compositions incorporate means to inhibit microbial growth, for example through preparation and packaging under sterile conditions and/or through inclusion of an antimicrobially effective amount of an ophthalmically acceptable preservative.

Suitable preservatives non-restrictively include mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

It is much preferred, where a preservative is present in an aqueous composition of the invention, to select a preservative that does not precipitate but remains in solution in the composition. Several preservatives can precipitate in the presence of other excipients in the composition and/or in the presence of the oxazolidinone drug. For example, benzalkonium chloride, disclosed for example as a component of an in situ gelling ophthalmic composition in above-cited European Patent No. 0 424 043, has been found to precipitate in a composition using iota-carrageenan as a gelling agent. Preferred preservatives, such as imidazolidinyl urea, methylparaben, propylparaben, phenoxyethanol, disodium EDTA, thimerosal, chlorobutanol and sorbic acid do not present this problem at concentrations useful herein and are especially desirable for in situ gellable aqueous solution compositions of the invention.

The term "in situ gellable" herein is to be understood as embracing not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye. Indeed, it can be advantageous to formulate a composition of the invention as a gel, to minimize loss of the composition immediately upon administration, as a result for example of lacrimation caused by reflex blinking. Although it is preferred that such a composition exhibit further increase in viscosity or gel stiffness upon administration, this is not absolutely required if the initial gel is sufficiently resistant to dissipation by lacrimal drainage to provide the effective residence time specified herein.

In a particular embodiment the composition is an in situ gellable aqueous solution, suspension or solution/suspension having excipients substantially as disclosed in above-cited U.S. Pat. No. 5,192,535, comprising about 0.1% to about 6.5%, preferably about 0.5% to about 4.5%, by weight, based on the total weight of the composition, of one or more lightly cross-linked carboxyl-containing polymers, and preferably having the oxazolidinone drug in solution. Such an aqueous composition has a pH of about 3 to about 6.5, preferably about 4 to about 6. A preferred polymer in this embodiment is polycarbophil, which causes the composition to gel upon contact with lacrimal fluid in the eye, which has a typical pH of about 7.2 to about 7.4. This formation of a gel enables the composition to remain in the eye for a prolonged period without loss by lacrimal drainage.

In another particular embodiment the composition is an in situ gellable aqueous solution, suspension or solution/suspension having excipients substantially as disclosed in above-cited U.S. Pat. No. 4,861,760, comprising about 0.1% to about 2% by weight of a polysaccharide that gels when it contacts an aqueous medium having the ionic strength of lacrimal fluid. A preferred such polysaccharide is gellan gum, more preferably a low acetyl clarified grade of gellan gum such as that sold under the trademark Gelrite®. Suitable partially deacylated gellan gums are disclosed in U.S. Pat. No. 5,190,927 to Chang & Kobzeff, incorporated herein by reference. Preferably the drug is in solution in the composition.

In another particular embodiment the composition is an in situ gellable aqueous solution, suspension or solution/suspension having excipients substantially as disclosed in above-cited U.S. Pat. No. 5,587,175, comprising about 0.2% to about 3%, preferably about 0.5% to about 1%, by weight of a gelling polysaccharide, preferably selected from gellan gum, alginate gum and chitosan, and about 1% to about 50% of a water-soluble film-forming polymer, preferably selected from alkylcelluloses (e.g., methylcellulose, ethylcellulose), hydroxyalkylcelluloses (e.g., hydroxyethylcellulose, hydroxypropyl methylcellulose), hyaluronic acid and salts thereof, chondroitin sulfate and salts thereof, polymers of acrylamide, acrylic acid and polycyanoacrylates, polymers of methyl methacrylate and 2-hydroxyethyl methacrylate, polydextrose, cyclodextrins, polydextrin, maltodextrin, dextran, polydextrose, gelatin, collagen, natural gums (e.g., xanthan, locust bean, acacia, tragacanth and carrageenan gums and agar), polygalacturonic acid derivatives (e.g., pectin), polyvinyl alcohol, polyvinylpyrrolidone and polyethylene glycol. The composition can optionally contain a gel-promoting counterion such as calcium in latent form, for example encapsulated in gelatin. Preferably the drug is in solution in the composition.

In another particular embodiment the composition is an in situ gellable aqueous solution, suspension or solution/suspension having excipients substantially as disclosed in above-cited European Patent No. 0 424 043, comprising about 0.1% to about 5% of a carrageenan gum. Carrageenans are sulfated polysaccharides; in this embodiment a carrageenan having no more than 2 sulfate groups per repeating disaccharide unit is preferred, including kappa-carrageenan, having 18–25% ester sulfate by weight, iota-carrageenan, having 25–34% ester sulfate by weight, and mixtures thereof. As indicated above, and contrary to the teaching of above-cited European Patent No. 0 424 043, where a preservative is to be included, it is preferred according to the present invention to select a preservative that does not precipitate in the composition.

In another particular embodiment the composition comprises a bioerodible polymer substantially as disclosed in above-cited U.S. Pat. No. 3,914,402.

In another particular embodiment the composition comprises an ophthalmically acceptable mucoadhesive polymer, selected for example from hydroxypropylmethylcellulose, carboxymethylcellulose, carbomer (acrylic acid polymer), poly(methylmethacrylate), polyacrylamide, polycarbophil, polyethylene oxide, acrylic acid/butyl acrylate copolymer, sodium alginate and dextran.

In another embodiment of the invention, the oxazolidinone antibacterial drug(s) are solubilized at least in part by an ophthalmically acceptable solubilizing agent. The term "solubilizing agent" herein includes agents that result in formation of a micellar solution or a true solution of the drug. Certain ophthalmically acceptable nonionic surfactants, for example polysorbate 80, can be useful as solubilizing agents, as can ophthalmically acceptable glycols, polyglycols, e.g., polyethylene glycol 400 (PEG-400), and glycol ethers.

A class of solubilizing agents having particular utility in solution and solution/suspension compositions of the invention is the cyclodextrins. Suitable cyclodextrins can be selected from α-cyclodextrin, β-cyclodextrin, γ-cyclodextrin, alkylcyclodextrins (e.g., methyl-β-cyclodextrin, dimethyl-β-cyclodextrin, diethyl-β- cyclodextrin), hydroxyalkylcyclodextrins (e.g., hydroxyethyl-β-cyclodextrin, hydroxypropyl-β-cyclodextrin), carboxyalkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed by Rajewski & Stella (1996), *Journal of Pharmaceutical Sciences,* 85, 1154, at pages 1155–1159. If desired, complexation of an oxazolidinone compound by a cyclodextrin can be increased by addition of a water-soluble polymer such as carboxymethylcellulose, hydroxypropyl methylcellulose or polyvinylpyrrolidone, as described by Loftsson (1998), *Pharmazie,* 53, 733–740.

An ophthalmically acceptable cyclodextrin can optionally be present in a composition of the invention at a concentration of about 1 to about 200 mg/ml, preferably about 5 to about 100 mg/ml and more preferably about 10 to about 50 mg/ml.

One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

One or more ophthalmically acceptable salts can be included in the composition in an amount required to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions; preferred salts include sodium chloride, potassium chloride, sodium thiosulfate, sodium bisulfite and ammonium sulfate, with sodium chloride being especially preferred.

Optionally one or more ophthalmically acceptable acids having at least two dissociable hydrogen groups can be included in a polymer-containing composition as interactive agents to retard release of the drug through inhibition of erosion of the polymer, as disclosed in International Patent Publication No. WO 95/03784, incorporated herein by reference. Acids useful as interactive agents include boric, lactic, orthophosphoric, citric, oxalic, succinic, tartaric and formic glycerophosphoric acids.

Optionally an ophthalmically acceptable xanthine derivative such as caffeine, theobromine or theophylline can be included in the composition, substantially as disclosed in U.S. Pat. No. 4,559,343 to Han & Roehrs, incorporated herein by reference. Inclusion of the xanthine derivative can reduce ocular discomfort associated with administration of the composition.

Optionally one or more ophthalmically acceptable surfactants, preferably nonionic surfactants, can be included in the composition to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Optionally one or more antioxidants can be included in the composition to enhance chemical stability where required. Suitable antioxidants include ascorbic acid and sodium metabisulfite.

One or more ophthalmic lubricating agents can optionally be included in the composition to promote lacrimation or as a "dry eye" medication. Such agents include polyvinyl alcohol, methylcellulose, hydroxypropyl methylcellulose, polyvinylpyrrolidone, etc. It will be understood that promotion of lacrimation is beneficial in the present invention only where lacrimation is naturally deficient, to restore a normal degree of secretion of lacrimal fluid. Where excessive lacrimation occurs, residence time of the composition in the eye can be reduced.

In one embodiment of the invention, an ion exchange resin in particulate form, for example a crosslinked styrene-divinylbenzene lattice resin with cationic or anionic functional groups, can be included in the composition, substantially as disclosed in U.S. Pat. No. 4,911,920 to Jani et al. or in U.S. Pat. No. 5,275,820 to Chang, both incorporated herein by reference. The oxazolidinone antibacterial drug, for example linezolid, can be reversibly loaded on to particles of the ion exchange resin; this can result in an extended duration of release of the drug to the treated eye.

In a presently preferred particular embodiment of the invention, the composition is an in situ gellable aqueous solution of an oxazolidinone antibacterial drug, most preferably linezolid, wherein the gelling agent is a carrageenan having on average about 1.5 to about 2 sulfate groups per repeating disaccharide unit. More preferably the gelling agent is iota-carrageenan, and is present in an amount of about 0.1% to about 2.5%, still more preferably about 0.2% to about 1%, and most preferably about 0.4% to about 0.8%, by weight. Iota-carrageenan gels in presence of divalent ions such as calcium ions, which are present in lacrimal fluid. Optionally but preferably a small amount of calcium in ionic form is included in the formulation to enhance gelling properties. Suitably the calcium can be introduced as a component of an iota-carrageenan product such as Sea-Spen™ of FMC.

If necessary, an appropriate amount of a calcium complexing agent such as ethylene diamine tetraacetic acid (EDTA) or a salt, for example the disodium salt, thereof, can be included in a composition of this particular embodiment to complex excess calcium ions and prevent gel formation during storage. EDTA or a salt thereof can suitably be included in an amount of about 0.01% to about 0.5%. Especially where a preservative other than EDTA is present, it is especially preferred to include EDTA or a salt thereof, more particularly disodium EDTA, in an amount of about 0.025% to about 0.1%, by weight, as synergistically enhanced antimicrobial activity can result.

A composition of this particular embodiment can optionally further comprise glycerin in an amount of about 0.5% to about 5%, more preferably about 1% to about 2.5%, for example about 1.5% to about 2%, by weight. Glycerin can be useful to increase viscosity of the composition and for adjustment of osmolality. Independently of the presence of glycerin, a composition of this particular embodiment can optionally further comprise a cyclodextrin, preferably hydroxypropyl-β-cyclodextrin, in an amount of about 0.5% to about 25% by weight. Such a cyclodextrin can be useful as a solubilizing agent as described above.

It is preferred that a composition of this particular embodiment contain an antimicrobially effective amount of a preservative. Illustratively, the composition can contain imidazolidinyl urea in an amount of about 0.03% to about 0.5%; methylparaben in an amount of about 0.015% to about 0.25%; propylparaben in an amount of about 0.005% to about 0.01%; phenoxyethanol in an amount of about 0.25% to about 1%; disodium EDTA in an amount of about 0.05% to about 0.2%; thimerosal in an amount of 0.001% to about 0.15%; chlorobutanol in an amount of about 0.1% to about 0.5%; and/or sorbic acid in an amount of about 0.05% to about 0.2%; all by weight.

The present invention also provides a method of treating or preventing both gram-positive and gram-negative bacterial infections in an eye, the method comprising topical application to the eye in co-therapy (including coformulation) of one or more oxazolidinone antibacterial drugs and one or more antibacterial drugs other than oxazolidinones effective against gram-negative organisms. The present invention also provides a pharmaceutical composition suitable for topical administration to an eye, the composition comprising as active agents (a) one or more oxazolidinone antibacterial drugs in a concentration effective for treatment and/or prophylaxis of a gram-positive bacterial infection of the eye, and (b) one or more antibacterial drugs other than oxazolidinones in a concentration effective for treatment and/or prophylaxis of a gram-negative bacterial infection of the eye.

Any ophthalmically acceptable gram-negative effective antibiotic can be used in such co-therapy or coformulation with one or more oxazolidinone antibiotics in accordance with this embodiment of the invention. Suitable gram-negative effective antibiotics can be selected, without limitation, from aminoglycosides, cephalosporins, diaminopyridines, fluroquinolones, sulfonamides and tetracyclines. Among particular antibiotics of these and other classes, each of the following may illustratively be useful as a gram-negative effective antibiotic: amikacin, azithromycin, cefixime, cefoperazone, cefotaxime, ceftazidime, ceftizoxime, ceftriaxone, chloramphenicol, ciprofloxacin, clindamycin, colistin, domeclocycline, doxycycline, erythromycin, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin and trimethoprim. Presently preferred gram-negative effective antibiotics are fluroquinolones such as ciprofloxacin, norfloxacin and ofloxacin, more particularly ciprofloxacin.

Preferably, such co-therapy or coformulation is with an oxazolidinone-containing composition as hereinabove described, i.e., having one or more ophthalmically acceptable excipient ingredients that reduce rate of removal of the composition from the eye by lacrimation such that the composition has an effective residence time in the eye of about 2 to about 24 hours. Any of the above-mentioned means for providing extended residence time can be used. For example, one can use a viscosity enhancer or a bioadhesive agent. More preferably, the formulation of the present invention includes a component, such as sodium carboxyl methyl cellulose, that acts both as a viscosity enhancer and as a bioadhesive agent. In a particularly preferred embodiment, the extended residence time is at least in part due to presence in the composition of an in situ gelling polymer system. It is especially preferred that both the oxazolidinone antibiotic component and the gram-negative effective antibiotic component are formulated to provide an effective residence time in the eye of about 2 to about 24 hours, and even more especially preferred that the two components are coformulated in the same composition having such an effective residence time. Such a coformulated composition represents a further embodiment of the present invention.

Compositions of the invention can be used in co-therapy with one or more drugs other than antibacterial agents. Such drugs other than antibacterial agents can be co-administered topically to the eye together with a composition of the invention. A composition of the invention can itself further comprise, in coformulation with a first active agent that comprises one or more oxazolidinone antibacterial agents, optionally together with one or more gram-negative effective antibacterial agents, a therapeutically and/or prophylactically effective amount of one or more drugs that are other than antibacterial agents. These drugs other than antibacterial agents can cooperate with the antibacterial drug(s) in treating and/or preventing an infective disease of the eye, or can be used to treat a related or unrelated condition simultaneously affecting the eye.

Any drug having utility as a topical ophthalmic application can be used in co-therapy, co-administration or coformulation with a composition of the invention as described immediately above. Such drugs include without limitation demulcents; antimycotics, antivirals and other anti-infectives; steroids, NSAIDs, selective cyclooxygenase-2 inhibitors and other anti-inflammatory agents; acetylcholine blocking agents; adrenergic agonists, beta-adrenergic blocking agents and other antiglaucoma agents; antihypertensives; antihistamines; anticataract agents; and topical and regional anesthetics. Illustrative specific drugs include acebutolol, aceclidine, acetylsalicylic acid (aspirin), $N^4$ acetylsulfisoxazole, alclofenac, alprenolol, amfenac, amiloride, aminocaproic acid, ρ-aminoclonidine, aminozolamide, anisindione, apafant, atenolol, bacitracin, benoxaprofen, benoxinate, benzofenac, bepafant, betamethasone, betaxolol, bethanechol, brimonidine, bromfenac, bromhexine, bucloxic acid, bupivacaine, butibufen, carbachol, carprofen, celecoxib, cephalexin, chloramphenicol, chlordiazepoxide, chlorprocaine, chlorpropamide, chlortetracycline, cicloprofen, cinmetacin, ciprofloxacin, clidanac, clindamycin, clonidine, clonixin, clopirac, cocaine, cromolyn, cyclopentolate, cyproheptadine, demecarium, dexamethasone, dibucaine, diclofenac, diflusinal, dipivefrin, dorzolamide, enoxacin, epinephrine, erythromycin, eserine, estradiol, ethacrynic acid, etidocaine, etodolac, fenbufen, fenclofenac, fenclorac, fenoprofen, fentiazac, flufenamic acid, flufenisal, flunoxaprofen, fluorocinolone, fluorometholone, flurbiprofen and esters thereof, fluticasone propionate, furaprofen, furobufen, furofenac, furosemide, gancyclovir, gentamicin, gramicidin, hexylcaine, homatropine, hydrocortisone, ibufenac, ibuprofen and esters thereof, idoxuridine, indomethacin, indoprofen, interferons, isobutylmethylxanthine, isofluorophate, isoproterenol, isoxepac, ketoprofen, ketorolac, labetolol, lactorolac, latanoprost, levo-bunolol, lidocaine, lonazolac, loteprednol, meclofenamate, medrysone, mefenamic acid, mepivacaine, metaproterenol, methanamine, methylprednisolone, metiazinic, metoprolol, metronidazole, minopafant, miroprofen, MK-663, modipafant, nabumetome, nadolol, namoxyrate, naphazoline, naproxen and esters thereof, neomycin, nepafenac, nitroglycerin, norepinephrine, norfloxacin, nupafant, olfloxacin, olopatadine, oxaprozin, oxepinac, oxyphenbutazone, oxyprenolol, oxytetracycline, parecoxib, penicillins, perfloxacin, phenacetin, phenazopyridine, pheniramine, phenylbutazone, phenylephrine, phenylpropanolamine, phospholine, pilocarpine, pindolol, pirazolac, piroxicam, pirprofen, polymyxin, polymyxin B, prednisolone, prilocaine, probenecid, procaine, proparacaine, protizinic acid, rimexolone, rofecoxib, salbutamol, scopolamine, sotalol, sulfacetamide, sulfanilic acid, sulindac, suprofen, tenoxicam, terbutaline, tetracaine, tetracycline, theophyllamine, timolol, tobramycin, tolmetin, triamcinolone, trimethoprim, trospectomycin, valdecoxib, vancomycin, vidarabine, vitamin A, warfarin, zomepirac and pharmaceutically acceptable salts thereof.

Compositions of the present invention can be prepared by methods known in the art and described in patents and publications cited herein and incorporated herein by reference.

Aqueous suspension compositions of the invention can be packaged in single-dose non-reclosable containers. Such containers can maintain the composition in a sterile condition and thereby eliminate need for preservatives such as mercury-containing preservatives, which can sometimes cause irritation and sensitization of the eye. Alternatively, multiple-dose reclosable containers can be used, in which case it is preferred to include a preservative in the composition.

In a method of the invention, a composition as herein described is administered topically in an antibacterially effective amount to an eye that is infected by one or more gram-positive bacterial organisms. The eye is of a warm-blooded, preferably mammalian subject. Suitable mammalian subjects include domestic, farm and exotic mammals, and humans. The method can be useful, for example, in treatment of eye infections of dogs, cats, horses, cattle, sheep and pigs, but is more particularly useful where the subject is human.

In a preferred method, the gram-positive bacterial organism(s) are species of Staphylococcus (e.g., *Staphylococcus aureus, Staphylococcus epidermidis*), Streptococcus (e.g., *Streptococcus viridans, Streptococcus pneumoniae*), Enterococcus, Bacillus, Corynebacterium, Propionibacterium, Chlamydia, Moraxella, Haemophilus and Neisseria. In an especially preferred method, the gram-positive bacterial organism(s) are of strain(s) that have developed significant levels of resistance to antibacterial agents other than the oxazolidinone antibacterial agent(s), e.g., linezolid, in the composition being administered.

Treatment of bacterial conjunctivitis by the method of the invention is appropriate, for example, where infection with one or more of the following species is present: *Staphylococcus aureus, Staphylococcus epidermidis, Streptococcus pneumoniae, Streptococcus pyogenes, Streptococcus viridans, Enterococcus faecalis*, Corynebacterium sp., Propionibacterium sp., Moraxella catarrhalis and *Haemophilus influenzae*.

Treatment of bacterial blepharitis by the method of the invention is appropriate, for example, where infection with one or more of the following species is present: *Staphylococcus aureus, Staphylococcus epidermidis* and *Streptococcus pneumoniae*.

Treatment of bacterial keratitis by the method of the invention is appropriate, for example, where infection with one or more of the following species is present: *Staphylococcus aureus, Staphylococcus epidermidis, Streptococcus pneumoniae* and *Streptococcus viridans*.

Prophylaxis of bacterial infection of the eye prior to ocular surgery by the method of the invention is appropriate, for example, where a risk exists of infection with one or more of the following species: *Staphylococcus aureus, Staphylococcus epidermidis*, Corynebacterium sp. and Propionibacterium sp.

An appropriate dosage, frequency and duration of administration, i.e., treatment regimen, to be used in any particular situation will be readily determined by one of skill in the art without undue experimentation, and will depend, among other factors, on the particular oxazolidinone compound(s) present in the composition, on the particular ophthalmic infective condition being treated, on the age, weight and general physical condition of the subject, and on other medication being administered to the subject. It is preferred that response of the ophthalmic infective condition to treatment according to the present method be monitored and the treatment regimen be adjusted if necessary in light of such monitoring.

Frequency of administration is typically such that the dosing interval, i.e., the period of time between one dose and the next, during waking hours is about 2 to about 12 hours, more typically about 3 to about 8 hours, for example about 4 to about 6 hours. It will be understood by those of skill in the art that an appropriate dosing interval is dependent to some degree on the length of time for which the selected composition is capable of maintaining a concentration of the oxazolidinone antibiotic in the lacrimal fluid and/or in the target tissue (e.g., the conjunctiva) above the $MIC_{90}$. Ideally the concentration remains above the $MIC_{90}$ for at least 100% of the dosing interval. Where this is not achievable it is desired that the concentration should remain above the $MIC_{90}$ for at least about 60% of the dosing interval, in a worst case at least about 40% of the dosing interval.

EXAMPLES

The following examples illustrate aspects of the present invention but are not to be construed as limitations. All percentages are by weight.

Example 1

Six formulations A–F were prepared, each containing 2 mg/ml linezolid in aqueous solution, for testing in guinea pig eyes to assess retention of linezolid in the exterior of the eye. In 1 ml of each formulation, 0.5 mg of the linezolid was $^{14}C$-labeled and 1.5 mg was unlabeled.

Formulation A was a solution of linezolid in normal saline.

Formulation B contained 2.6% glycerin.

Formulation C contained 0.2% xanthan gum and 12.5% hydroxypropyl-β-cyclodextrin.

Formulation D contained 0.5% hydroxypropylmethylcellulose (HPMC), 7% hydroxypropyl-β-cyclodextrin and 0.78% sodium chloride.

Formulation E contained 17% poloxamer 407 (a polyoxyethylene-polyoxypropylene-polyoxyethylene block copolymer, supplied as Pluronic™ F-127 of BASF) and 3.5% hydroxypropyl-β-cyclodextrin.

Formulation F contained 0.5% polycarbophil, supplied as Noveon™ AA-1 of B.F.Goodrich.

Eight healthy male guinea pigs of body weight 150 to 200 g were assigned to treatment with each formulation. To each of the eyes of each guinea pig, 5 µl of the test formulation was applied using a micropipette. Guinea pigs were sacrificed 0.25, 1, 2 and 4 hours after application, and eye tissues were excised. Eyeballs were rinsed with saline to collect unabsorbed drug. The resulting rinsate was combusted for liquid scintillation counting to determine radioactivity as a measure of amount of linezolid remaining in the exterior of the eye. Results are presented in FIG. 1.

It will be seen in FIG. 1 that only very small amounts of linezolid were retained in the exterior of treated eyes one hour or more after application of formulations A and B. It is unlikely that either of these formulations will have an effective residence time in the eye as defined herein of 2 hours or more. By contrast, treatment with formulations C–F, all of which contained a gelling or mucoadhesive agent (xanthan gum, HPMC, poloxamer 407 and polycarbophil respectively), resulted in significant amounts of linezolid being retained in the exterior of treated eyes one hour or more after application. The data shown in FIG. 1 therefore demonstrate enhanced residence time in the eye for formulations containing a gelling or mucoadhesive agent.

Example 2

Five formulations G–L were prepared, each containing 2.5 mg/ml linezolid in aqueous solution, for testing in rabbit eyes to assess the concentration of linezolid found in lacrimal fluid, cornea and conjunctiva, 0.5 and 1 hour after application. In 1 ml of each formulation, 0.5 mg of the linezolid was $^{14}$C-labeled and 2 mg was unlabeled. Formulation G was a 2.5 mg/l solution of linezolid in normal saline, included in the study for comparative purposes. Compositions of formulations H–L were as indicated below. Iota-carrageenan was supplied as Gelcarin™ GP379-NF of FMC; iota-carrageenan with calcium was supplied as Sea-Spen™ of FMC.

| Formulation H | |
|---|---|
| Linezolid | 0.25% |
| Sodium alginate | 2% |
| PEG-400 | 10% |
| Water | to 100% |
| Formulation I | |
| Linezolid | 0.25% |
| Sodium alginate | 1.3% |
| PEG-400 | 5% |
| Polyethylene oxide | 0.5% |
| Water | to 100% |
| Formulation J | |
| Linezolid | 0.25% |
| Iota-carrageenan | 0.5% |
| Glycerin | 2% |
| Water | to 100% |
| Formulation K | |
| Linezolid | 0.25% |
| Iota-carrageenan | 0.5% |
| Iota-carrageenan with calcium | 0.3% |
| Glycerin | 1.5% |
| Disodium EDTA dihydrate | 0.04% |
| Water | to 100% |
| Formulation L | |
| Linezolid | 0.25% |
| Iota-carrageenan | 0.5% |
| PEG-400 | 0.5% |
| HPMC | 2% |
| Water | to 100% |

Note: the polyethylene oxide in formulation I had an average molecular weight of about 4,000,000.

Twelve healthy male New Zealand white rabbits of body weight 1.8 to 2.5 kg were assigned to treatment with each formulation. To each of the eyes of each rabbit, 25 µl of the test formulation was applied using a pipette. Rabbits were sacrificed 0.5 and 1 hour after application, and eye tissues were excised. Just prior to sacrifice, lacrimal fluid was collected from each eye. Conjunctival and corneal tissues were excised following sacrifice. The lacrimal fluid and excised tissues were combusted for liquid scintillation counting to determine radioactivity as a measure of amount of linezolid present. Radioactive counts were converted by calculation to concentration of linezolid in µg/g. Results are presented in FIGS. 2–4.

Figure 2:
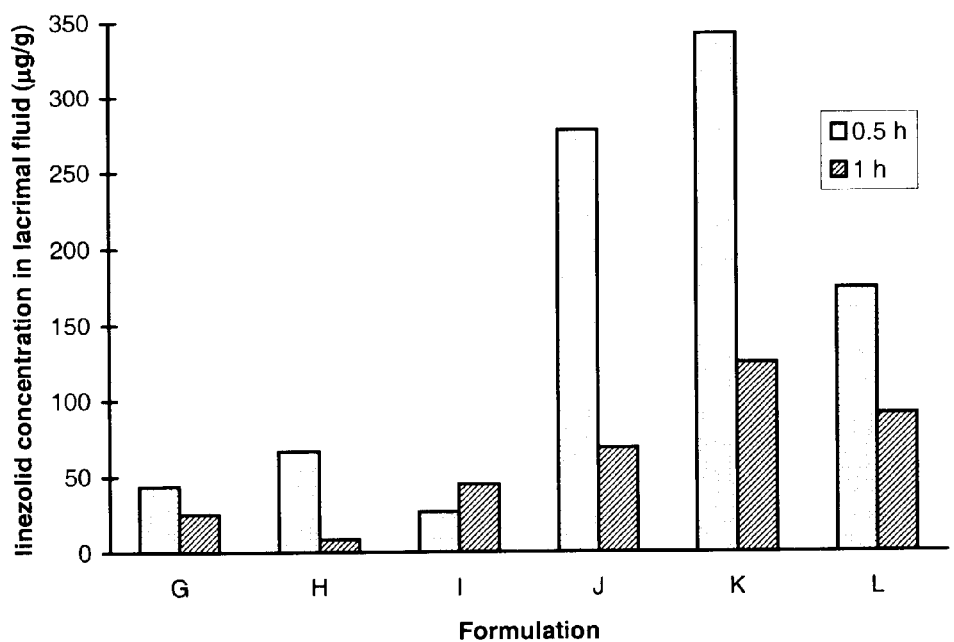
FIG. 2 is a graphical representation of data from Example 2, showing concentrations of linezolid in lacrimal fluid of rabbit eyes 0.5 h and 1 h after treatment with linezolid formulations G–L as described herein.
Figure 3:
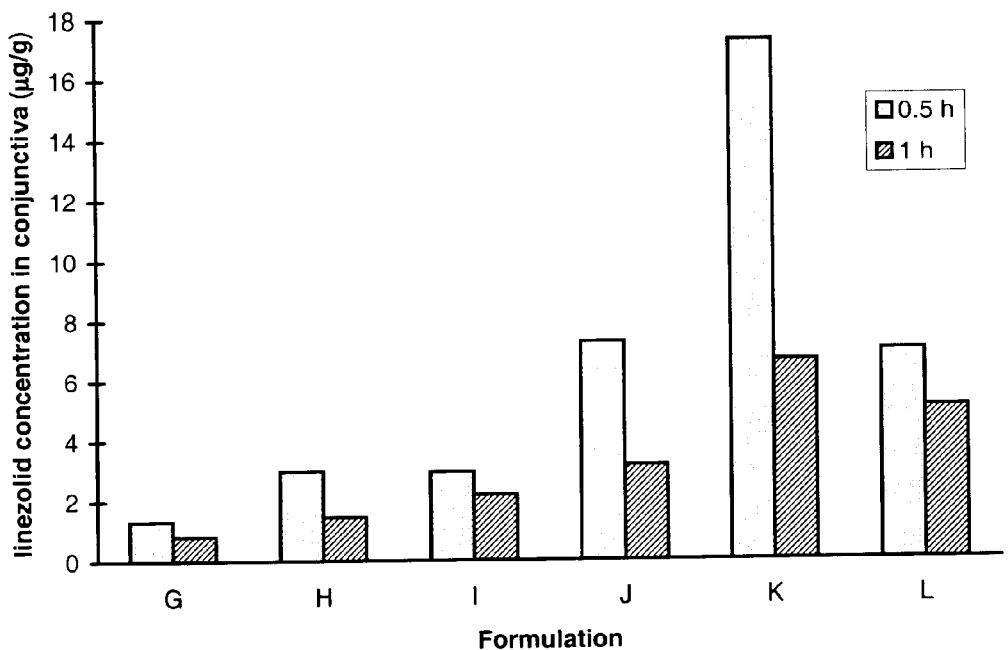
FIG. 3 is a graphical representation of data from Example 2, showing concentrations of linezolid in the conjunctiva of rabbit eyes 0.5 h and 1 h after treatment with linezolid formulations G–L as described herein.
Figure 4:
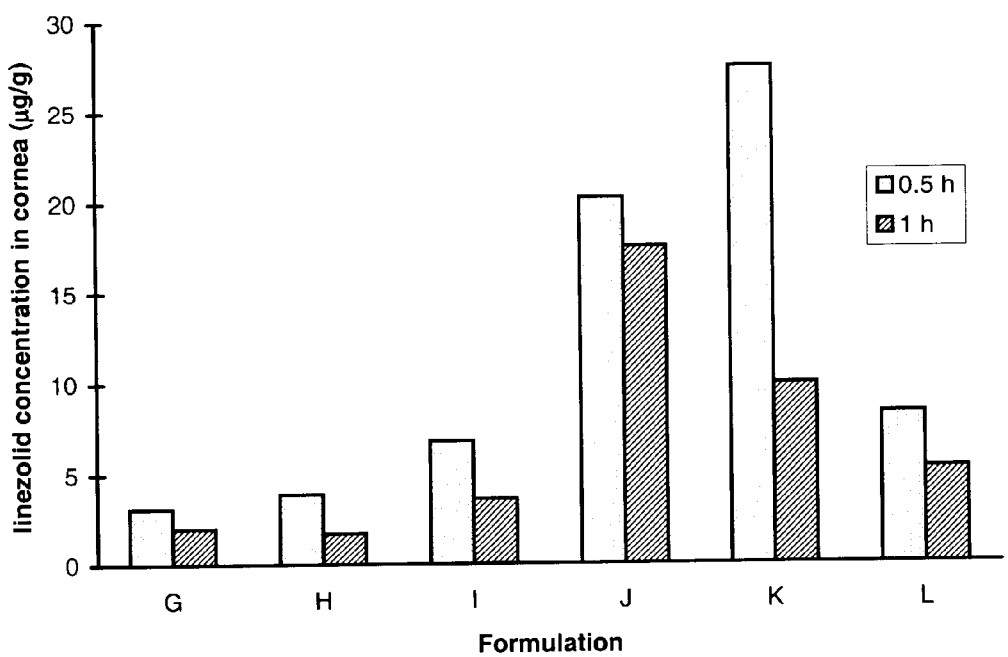
FIG. 4 is a graphical representation of data from Example 2, showing concentrations of linezolid in the cornea of rabbit eyes 0.5 h and 1 h after treatment with linezolid formulations G–L as described herein.

It will be seen in FIGS. 2–4 that formulations J, K and L provided higher concentrations of linezolid in lacrimal fluid, conjunctiva and cornea than formulations G, H and I. Each of formulations J, K and L contained as gelling agent iota-carrageenan, which is a preferred gelling agent for in situ gelling compositions of the present invention.

Example 3

Formulation M was prepared containing 50 mg/ml linezolid in aqueous solution. Formulation M was applied to rabbit eyes to assess the concentration of linezolid in the lacrimal fluid, cornea, and conjunctiva, 1 hour after application. In 1 ml of the formulation, 0.5 mg of linezolid was $C^{14}$-labeled, and 50 mg was unlabeled. The detailed compostion of formulation M is indicated below.

| Formulation M | |
|---|---|
| Linezolid | 5% |
| Sodium Carboxymethylcellulose | 1% |
| HydroxyPropyl-β-Cyclodextrin | 25% |

Four healthy male New Zealand white rabbits of body weight 1.8 to 2.5 kg were treated with the formulation, as follows. To each of the eyes of each rabbit, 25µl of the test formulation was applied using a pipette. Rabbits were sacrificed 1 hour after application, and eye tissues were excised. Just prior to sacrifice, lacrimal fluid was collected from each eye. Lacrimal fluid and excised tissues were combusted for liquid scintillation counting to determine radioactivity as a measure of amount of radioactivity present. Radioactive counts were converted into units of concentration of linezolid expressed in µg/g. The results are presented below.

| Linezolid concentration in µg/g in: | |
|---|---|
| Lacrimal Fluid | 2334 |
| Conjunctiva | 133 |
| Cornea | 48 |

The high amounts of linezolid absorbed into the eye upon application of formulation M is thought to be due, in part, to the presence of sodium carboxymethylcellulose, a viscosity enhancer and bioadhesive agent, in the formulation. The high absorptivity is also believed to be due to a high linezolid concentration in the formula, and to the presence of hydroxypropyl-β-cyclodextrin, a particularly preferred solubilizing agent.

What is claimed is:

1. A pharmaceutical composition suitable for topical administration to an eye, the composition comprising:

as active agent at least one oxazolidinone antibacterial drug in a concentration effective for treatment and/or prophylaxis of a gram-positive bacterial infection of at least one tissue of the eye, and at least one ophthalmically acceptable excipient that reduces a rate of removal of the composition from the eye by lacrimation, such that the composition has an effective residence time in the eye of about 2 to about 24 hours.

2. The composition of claim 1 wherein the at least one oxazolidinone antibacterial drug is a compound of formula

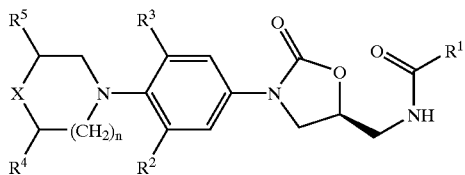

wherein:
- R¹ is selected from (a) H, (b) $C_{1-8}$ alkyl optionally substituted with at least one F, Cl, OH, $C_{1-8}$ alkoxy, and $C_{1-8}$ acyloxy or $C_{1-8}$ benzoxy, including a $C_{3-6}$ cycloalkyl group, (c) amino, (d) mono- and di($C_{1-8}$ alkyl)amino and (e) $C_{1-8}$ alkoxy groups;
- R² and R³ are independently selected from H, F and Cl groups;
- R⁴ is H or $CH_3$;
- R⁵ is selected from H, $CH_3$, CN, $CO_2R^1$ and $(CH_2)mR^6$ groups, where R¹ is as defined above, R⁶ is selected from H, OH, OR¹, OCOR¹, NHCOR¹, amino, mono- and di($C_{1-8}$ alkyl)amino groups, and m is 1 or 2;
- n is 0, 1 or 2; and
- X is O, S, SO, $SO_2$, $SNR^7$ or $S(O)NR^7$ where R⁷ is selected from H, $C_{1-4}$ alkyl (optionally substituted with one or more F, Cl, OH, $C_{1-8}$ alkoxy, amino, $C_{1-8}$ mono- or di($C_{1-8}$ alkyl)amino groups), and p-toluenesulfonyl groups;

or a pharmaceutically acceptable salt thereof.

3. The composition of claim 2 wherein, in said formula, R¹ is $CH_3$; R² and R³ are independently selected from H and F but at least one of R² and R³ is F; R⁴ and R⁵ are each H; n is 1; and X is selected from O, S and $SO_2$.

4. The composition of claim 1 wherein the at least one oxazolidinone antibacterial drug is selected from the group consisting of: linezolid, eperezolid, N-((5S)-3-(3-fluoro-4-(4-(2-fluoroethyl)-3-oxopiperazin-1-yl)phenyl)-2-oxooxazolidin-5-ylmethyl)acetamide, (S)-N-[[3-[5-(3-pyridyl)thiophen-2-yl]-2-oxo-5-oxazolidinyl]methyl] acetamide, (S)-N-[[3-[5-(4-pyridyl)pyrid-2-yl]-2-oxo-5-oxazolidinyl]methyl]acetamide hydrochloride and N-[[(5S)-3-[4-(1,1-dioxido-4-thiomorpholinyl)-3,5-difluorophenyl]-2-oxo-5-oxazolidinyl]methyl]acetamide.

5. The composition of claim 1 wherein the active agent comprises linezolid.

6. The composition of claim 1 wherein the active agent comprises N-[[(5S)-3-[4-(1,1-dioxido-4-thiomorpholinyl)-3,5-difluorophenyl]-2-oxo-5-oxazolidinyl]methyl] acetamide.

7. The composition of claim 1 that is in a form selected from a solution, a suspension, a solution/suspension, a gel, an ointment, and a solid article suitable for ocular implant.

8. The composition of claim 1 in the form of an in situ gellable material in a form selected from a solution, a suspension and a solution/suspension, wherein the in situ gellable material has an ophthalmically compatible pH and osmolality.

9. The composition of claim 8 wherein the active agent is in solution.

10. The composition of claim 8 that comprises about 0.1 to about 200 mg/ml of the at least one oxazolidinone antibacterial drug.

11. The composition of claim 8 that comprises about 0.5 to about 80 mg/ml of the at least one oxazolidinone antibacterial drug.

12. The composition of claim 8 that comprises as a gelling agent about 0.1% to about 2.5% by weight of a carrageenan comprising repeating disaccharide units having on average no more than about 2 sulfate groups per disaccharide unit.

13. The composition of claim 12 wherein the carrageenan is iota-carrageenan.

14. The composition of claim 12, further comprising an antimicrobially effective amount of a preservative.

15. The composition of claim 14 wherein the preservative is in solution in the composition.

16. The composition of claim 14 wherein the preservative is selected from imidazolidinyl urea, methylparaben, propylparaben, phenoxyethanol, disodium EDTA, thimerosal, chlorobutanol, sorbic acid and mixtures thereof.

17. The composition of claim 1, further comprising at least one antibacterial drug effective against gram-negative bacteria.

18. The composition of claim 17 wherein the at least one antibacterial drug effective against gram-negative bacteria are selected from the group consisting of amikacin, azithromycin, cefixime, cefoperazone, cefotaxime, ceftazidime, ceftizoxime, ceftriaxone, chloramphenicol, ciprofloxacin, clindamycin, colistin, domeclocycline, doxycycline, erythromycin, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin and trimethoprim.

19. The composition of claim 1, wherein the at least one ophthalmically acceptable excipient is a viscosity enhancer.

20. The composition of claim 19, wherein the viscosity enhancer is sodium carboxymethylcellulose.

21. A pharmaceutical composition suitable for topical administration to an eye, the composition comprising:
- as active agent at least one oxazolidinone antibacterial drug in a concentration effective for treatment and/or prophylaxis of a gram-positive bacterial infection of one or more tissues of the eye, and
- at least one ophthalmically acceptable excipient that reduces a rate of removal of the composition from the eye by lacrimation such that a concentration of the active agent in lacrimal fluid of the eye is maintained above the $MIC_{90}$ for at least about 2 hours following topical application to the eye.

22. A method of treating and/or preventing a bacterial infection in an eye of a warm-blooded subject, the method comprising:
- administering in each of one or more topical applications to the eye a therapeutically or prophylactically effective amount of a composition comprising as active agent at least one oxazolidinone antibacterial drug and at least one ophthalmically acceptable excipient that reduces a rate of removal of the composition from the eye by lacrimation such that the composition has an effective residence time in the eye of about 2 to about 24 hours.

23. The method of claim 22, wherein the warm-blooded subject is a human subject.

24. The method of claim 23, wherein the topical administration to the eye is done in co-therapy with the at least one oxazolidinone antibacterial drug, at least one antibacterial drug effective against gram-negative bacteria.

25. The method of claim 24 wherein the at least one antibacterial drug effective against gram-negative bacteria is selected from the group consisting of amikacin, azithromycin, cefixime, cefoperazone, cefotaxime, ceftazidime, ceftizoxime, ceftriaxone, chloramphenicol, ciprofloxacin, clindamycin, colistin, domeclocycline, doxycycline, erythromycin, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin, and trimethoprim.

26. The method of claim 23, wherein the topical administration to the eye is done in co-therapy with the oxazolidinone antibacterial drug(s), one or more drug(s) selected from acebutolol, aceclidine, acetylsalicylic acid, $N^4$ acetylsulfisoxazole, alclofenac, alprenolol, amfenac, amiloride, aminocaproic acid, ρ-aminoclonidine, aminozolamide, anisindione, apafant, atenolol, bacitracin, benoxaprofen, benoxinate, benzofenac, bepafant, betamethasone, betaxolol, bethanechol, brimonidine, bromfenac, bromhexine, bucloxic acid, bupivacaine, butibufen, carbachol, carprofen, celecoxib, cephalexin, chloramphenicol, chlordiazepoxide, chlorprocaine, chlorpropamide, chlortetracycline, cicloprofen, cinmetacin, ciprofloxacin, clidanac, clindamycin, clonidine, clonixin, clopirac, cocaine, cromolyn, cyclopentolate, cyproheptadine, demecarium, dexamethasone, dibucaine, diclofenac, diflusinal, dipivefrin, dorzolamide, enoxacin, epinephrine, erythromycin, eserine, estradiol, ethacrynic acid, etidocaine, etodolac, fenbufen, fenclofenac, fenclorac, fenoprofen, fentiazac, flufenamic acid, flufenisal, flunoxaprofen, fluorocinolone, fluorometholone, flurbiprofen and esters thereof, fluticasone propionate, furaprofen, furobufen, furofenac, furosemide, gancyclovir, gentamicin, gramicidin, hexylcaine, homatropine, hydrocortisone, ibufenac, ibuprofen and esters thereof, idoxuridine, indomethacin, indoprofen, interferons, isobutylmethylxanthine, isofluorophate, isoproterenol, isoxepac, ketoprofen, ketorolac, labetolol, lactorolac, latanoprost, levo-bunolol, lidocaine, lonazolac, loteprednol, meclofenamate, medrysone, mefenamic acid, mepivacaine, metaproterenol, methanamine, methylprednisolone, metiazinic, metoprolol, metronidazole, minopafant, miroprofen, MK-663, modipafant, nabumetome, nadolol, namoxyrate, naphazoline, naproxen and esters thereof, neomycin, nepafenac, nitroglycerin, norepinephrine, norfloxacin, nupafant, olfloxacin, olopatadine, oxaprozin, oxepinac, oxyphenbutazone, oxyprenolol, oxytetracycline, parecoxib, penicillins, perfloxacin, phenacetin, phenazopyridine, pheniramine, phenylbutazone, phenylephrine, phenylpropanolamine, phospholine, pilocarpine, pindolol, pirazolac, piroxicam, pirprofen, polymyxin, polymyxin B, prednisolone, prilocaine, probenecid, procaine, proparacaine, protizinic acid, rimexolone, rofecoxib, salbutamol, scopolamine, sotalol, sulfacetamide, sulfanilic acid, sulindac, suprofen, tenoxicam, terbutaline, tetracaine, tetracycline, theophyllamine, timolol, tobramycin, tolmetin, triamcinolone, trimethoprim, trospectomycin, valdecoxib, vancomycin, vidarabine, vitamin A, warfarin, zomepirac, and pharmaceutically acceptable salts thereof.

27. A method of treating and/or preventing a bacterial infection in an eye of a warm-blooded subject, the method comprising:

administering in at least one topical applications to the eye a therapeutically or prophylactically effective amount of a composition comprising as active agent at least one oxazolidinone antibacterial drug and at least one ophthalmically acceptable excipient that reduces a rate of removal of the composition from the eye by lacrimation such that a concentration of the active agent in lacrimal fluid of the eye is maintained above the $MIC_{90}$ for at least about 2 hours following topical application to the eye.

28. A method of use of a composition in manufacture of a medicament for topically treating or preventing a gram-positive bacterial infection in an eye, the composition comprising as active agent at least one oxazolidinone antibacterial drug and at least one ophthalmically acceptable excipient that reduces a rate of removal of the composition from the eye by lacrimation such that the composition has an effective residence time in the eye of about 2 to about 24 hours.

29. A pharmaceutical composition suitable for topical administration to an eye, the composition comprising:

as active agents (a) at least one oxazolidinone antibacterial drug in a concentration effective for treatment and/or prophylaxis of a gram-positive bacterial infection of the eye, and (b) at least one antibacterial drug other than an oxazolidinone in a concentration effective for treatment and/or prophylaxis of a gram-negative bacterial infection of the eye.

* * * * *